United States Patent [19]

Roldan et al.

[11] 3,962,243

[45] June 8, 1976

[54] MEPYRAMINE THEOPHYLLINE ACETATE

[75] Inventors: Cristobal Martinez Roldan; Miguel Fernandez Braña; Jose Maria Castellano Berlanga, all of Madrid, Spain

[73] Assignee: Laboratories Made, S.A., Madrid, Spain

[22] Filed: Oct. 16, 1974

[21] Appl. No.: 515,188

Related U.S. Application Data

[63] Continuation-in-part of Ser. No. 396,426, Sept. 12, 1973, abandoned.

[52] U.S. Cl. .................................. 260/253; 424/253
[51] Int. Cl.² ..................................... C07D 473/08
[58] Field of Search ..................................... 260/253

[56] References Cited
UNITED STATES PATENTS

| | | | |
|---|---|---|---|
| 2,534,235 | 12/1950 | Cusic | 260/253 |
| 2,942,000 | 6/1960 | Mizier | 260/253 |
| 3,098,854 | 7/1963 | Klosa | 260/253 |
| 3,190,920 | 6/1965 | Spickett et al. | 260/253 |

*Primary Examiner*—Paul M. Coughlan, Jr.
*Attorney, Agent, or Firm*—Woodhams, Blanchard and Flynn

[57] ABSTRACT

The 7-theophylline acetic acid salt of mepyramine possesses bronchial spasmolytic, antiarrhythmic, cerebral oxidation inhibitor and platelet aggregation inhibitor properties. It is prepared by slowly adding a solution of mepyramine to a suspension of 7-theophylline acetic acid in the same solvent to effect the salt-forming reaction. It can be incorporated in various pharmaceutical unit dosage forms.

1 Claim, No Drawings

MEPYRAMINE THEOPHYLLINE ACETATE

CROSS-REFERENCE TO RELATED APPLICATION

This application is a continuation-in-part of U.S. patent application Ser. No. 396,426, filed Sept. 12, 1973, now abandoned, the entire contents of which are incorporated herein by reference.

This invention relates to a novel mepyramine salt possessing pharmacological activity, in particular as a bronchial spasmolytic, an antiarrhythmic, a cerebral oxidation inhibitor and a platelet aggregation inhibitor.

Mepyramine, 2-[(2-dimethylaminoethyl) (p-methoxybenzyl)amino]-pyridine, is well known as an antihistamine. We have found that its salt with 7-theophylline acetic acid, a known diuretic, smooth muscle relaxant and myocardial stimulant, possesses a number of advantages and additional pharmacological utilities in comparison with the precursor compounds.

According to the present invention we provide 2-[(2-dimethylaminoethyl) (p-methoxybenzyl)amino]-pyridine 1,2,3,6-tetrahydro-1,3-dimethyl-2,6-dioxopurin-7-acetate, having the formula

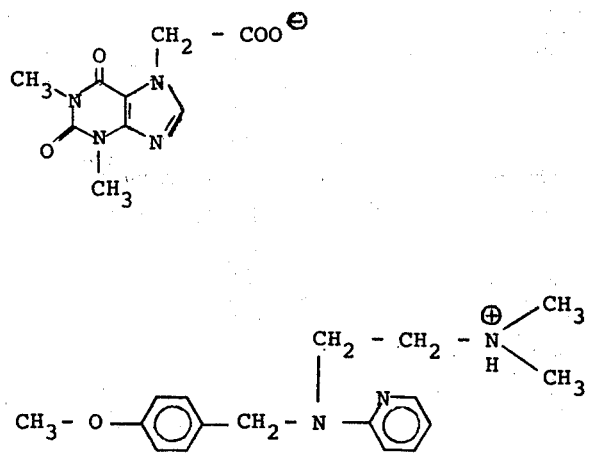

The activities and advantages of the novel compound according to the invention, referred to hereinafter as mepyramine theophylline acetate, appear from the following description:

1. Protective action against histamine-induced death

Histamine (1 mg every 5 minutes i.p.) administered to guinea pigs causes death when a total of 17 mg. of histamine has been administered. In our tests, previous treatment of the test animals with mepyramine theophylline acetate (1.5 mg/kg) raises the lethal dose of histamine in the above test to 51 mg.

2. Antihistamine action

The $pA_2$ of mepyramine theophylline acetate in isolated guinea pig ileum is found to be 10.05.

3. Anticholinergic Action

The action of acetylcholine on isolated guinea pig ileum is found to be inhibited at doses of 2.5 mcg/ml of mepyramine theophylline acetate.

4. Bronchial spasmolytic action a. Effective action against bronchial spasm is obtainable by all routes (oral, rectal, intramuscular and intravenous).

b. The compound is active in very small doses (6 mcg/kg).

c. The compound is found to have a long duration of activity (over 5 hours).

5. Antiarrhythmic action

Mepyramine theophylline acetate in concentrations of $4.6 \times 10^{-5}$ M and $9 \times 10^{-5}$ M produces an intense antiarrhythmic action in isolated guinea pig heart which can almost be compared with the action of $\beta$-blocking agents.

6. Action on cerebral oxidative activity

In concentrations of $1 \times 10^{-3}$ and $1 \times 10^{-4}$ M mepyramine theophylline acetate produces a strong inhibition of the oxygen consumption in rat complete brain homogenates.

7. Action on platelet aggregation

Mepyramine theophylline acetate is believed to activate the adenyl-cyclase system with accumulation of intracellular cyclic AMP and as a result it inhibits the aggregation and adhesion of the platelets. In comparative in vitro experiments it has been shown that this substance has the most potent activity in this respect, being active at concentrations as small as $1 \times 10^{-8}$M. The only substance reported in the literature as having a higher activity is prostaglandin E ($PGE_1$) which is active in concentrations of $1 \times 10^{-7}$M. $PGE_1$ however is very labile as compared with mepyramine theophylline acetate which is quite stable.

8. Toxicology

1. Acute toxicity

In white mice of the Swiss ICR strain

|  | $LD_{50}$ |
|---|---|
| Oral route | 234 mg/kg |
| Intravenous route | 55.7 mg/kg |
| Intraperitoneal route | 116.6 mg/kg |

2. Sub-acute and chronic toxicity

No microscopic or macroscopic organ alteration has been observed after administration of the product to mice over periods of 2 and 6 months.

9. Indications

Mepyramine theophylline acetate is thus indicated as a bronchial spasmolytic, an antiarrhythmic and an antithrombotic agent.

According to a further feature of the present invention, we provide pharmaceutical compositions comprising as an active ingredient 2-[(2-dimethylaminoethyl) (p-methoxybenzyl)amino]-pyridine 1,2,3,6-tetrahydro-1,3-dimethyl-2,6-dioxopurin-7-acetate in association with one or more compatible pharmaceutical carriers or excipients.

The compositions can be formulated for administration by oral, rectal, intramuscular or intravenous routes. The compositions can thus be in the form of tablets, coated tablets, capsules, granules, syrups, elixirs, solutions for injection and suppositories. The compositions can contain conventional pharmacologically acceptable carriers and excipients such as starch, magnesium stearate, lactose, talc, cocoa-butter and other fatty acid glycerides and stabilizing, flavouring and colouring agents as desired.

The dosage varies, of course, depending on the route of administration and the clinical indications. Typical daily doses in adult humans are 210 mg to 900 mg (oral), 600 mg to 1800 mg (rectal), 1.6 mg to 14 mg (intravenous) and 1.6 mg to 30 mg (intramuscular).

The compositions are preferably formulated as dosage units, each unit comprising a standard measured amount of the active compound. Typical dosage unit forms include: capsules and tablets, each containing from 75 to 150 mg of active compound, preferably 150 mg per capsule or tablet; oral solutions, each teaspoon of 5 ml containing 12.5–25 mg of active compound, preferably 25 mg per spoonful; oral solution "drops", each drop contains approximately 0.5 to 2 mg of active compound, preferably 1 mg per drop; ampoules for injection, each containing 0.75 to 5 mg of active compound in 4 ml of vehicle, preferably 5 mg perampoule; suppositories, each containing 25 to 300mg of active compound, preferably 300 mg per suppository.

According to a further feature of the present invention we provide a process for the preparation of the compound according to the invention wherein 2-[(2-dimethylaminoethyl)(p-methoxybenzyl)amino]-pyridine in solution is added slowly to a suspension of 1,2,3,6-tetrahydro-1,3-dimethyl-2,6-dioxopurin-7-acetic acid in the same solvent. The solvent is preferably a volatile alcohol such as ethanol. The reaction mixture may be heated if required to aid solution and should preferably be filtered before the product is isolated by evaporating to dryness. The product obtained in this way may be purified by lyophilizing an aqueous solution. A white crystalline product melting at 65°C (without melting point correction) can be obtained. The product is soluble in water and in alcohol and is quite hygroscopic.

The following Examples illustrate the invention further.

EXAMPLE 1

2-[(2-dimethylaminoethyl) (p-methoxybenzyl)amino]-pyridine (5.70 g, 0.02 mole) dissolved in ethanol (10 ml) is added slowly to a hot suspension of 1,2,3,6-tetrahydro-1,3-dimethyl-2,6-dioxopurin-7-acetic acid (4.7 g, 0.02 mole) in ethanol (50 ml). The mixture is shaken for 10 minutes, filtered and the filtrate is then evaporated to dryness in a rotary evaporator, the bath temperature not being allowed to exceed 50°C. The product obtained was a colourless candy-like solid which was dissolved in water and lyophilized to obtain a pure white crystalline product. MP 65°C (without correction).

Analysis. Calculated for $C_{26}H_{33}N_7O_5$: C: 59.64; H: 6.36; N: 18.72%. Found: C: 59.44; H: 6.53; N: 18.94%.

We show below illustrative examples of pharmacological compositions in which the active ingredient is 2-[(2-dimethylaminoethyl) (p-methoxybenzyl)amino]-pyridine 1,2,3,6-tetrahydro-1,3-dimethyl-2,6-dioxopurin-7-acetate, associated to pharmaceutical excipients and vehicles.

EXAMPLE 2

Pharmaceutical composition for an oral solution to be dosed in spoonfuls, e.g., 2.5 ml, 5 ml and 10 ml.

| Composition per 100 ml bottle. | |
|---|---|
| 2-[(2-dimethylaminoethyl)(p-methoxybenzyl)amino]-pyridine 1,2,3,6-tetrahydro-1,3-dimethyl-2,6-dioxopurin-7-acetate | 500 mg. |
| sodium phosphate, monobasic($NaH_2PO_4.H_2O$) | 258.7 mg. |
| sodium phosphate, dibasic anhydrous ($Na_2HPO_4$) | 113.6 mg. |
| methyl p-hydroxybenzoate | 30.0 mg. |
| ethyl p-hydroxybenzoate | 10.0 mg. |
| sodium metabisulfite | 50.0 mg. |
| saccharin | 20.0 mg. |
| sorbitol | 33.3 g. |
| propyleneglycol | 6.6 g. |
| distilled water, to make | 100.0 ml. |

EXAMPLE 3

Pharmaceutical composition for an oral solution to be dosed in drops.

| Composition per 10 ml bottle. | |
|---|---|
| 2-[(2-dimethylaminoethyl)(p-methoxybenzyl)amino]-pyridine 1,2,3,6-tetrahydro-1,3-dimethyl-2,6-dioxopurin-7-acetate | 200 mg. |
| $NaH_2PO_4.H_2O$ | 103.12 mg. |
| $Na_2HPO_4$ | 45.44 mg. |
| saccharin | 10 mg. |
| methyl p-hydroxybenzoate | 4 mg. |
| propyl p-hydroxybenzoate | 2 mg. |
| propyleneglycol | 5 ml. |
| distilled water, to make | 10 ml. |

EXAMPLE 4

Pharmaceutical composition for a solution to be administered intravenously.

| Composition per 100 ml of injectable solution | |
|---|---|
| 2-[(2-dimethylaminoethyl)(p-methoxybenzyl)amino]-pyridine 1,2,3,6-tetrahydro-1,3-dimethyl-2,6-dioxopurin-7-acetate | 1.2500 g. |
| $NaH_2PO_4.H_2O$ | 0.6445 g. |
| $Na_2HPO_4$ | 0.2840 g. |
| sodium chloride | 9.0 g |
| water for injections, to make | 1,000 ml. |

This solution can be incorporated in 1 ml, 2 ml and 4 ml ampoules containing 1.25 mg, 2.5 mg and 5 mg respectively of active ingredient per ampoule.

EXAMPLE 5

Pharmaceutical composition of powder to be administered in capsules.

| Composition per 100 g. of powder | |
|---|---|
| 2-[(2-dimethylaminoethyl)(p-methoxybenzyl)amino]-pyridine 1,2,3,6-tetrahydro-1,3-dimethyl-2,6-dioxopurin-7-acetate | 49.02 g. |
| mannitol | 49.02 g. |
| magnesium stearate | 1.96 g. |

Instead of mannitol another excipient such as lactose, starch, etc., can be used or even anhydrous silicon (slow release capsules).

Hard gelatine capsules No. 0, 2 or 3 are filled with powder. Each capsule will contain 150, 100 and 75 mg., respectively, of active ingredient.

EXAMPLE 6

Pharmaceutical composition of a mass to be administered through rectal route.

| Composition per 100 g. of mass | |
|---|---|
| 2-[(2-dimethylaminoethyl)(p-methoxybenzyl)-amino]-pyridine 1,2,3,6-tetrahydro-1,3-dimethyl-2,6-dioxopurin-7-acetate | 5.85 g. |
| Mass Henkel G 34/36 special | 94.15 g. |

Suppositories of 1.710 g. of weight are made from the mass. Each suppository will contain 0.100 mg. of active ingredient.

By changing the proportions of the excipients, suppositories with 25 and 300 mg. of active ingredients can be made.

The embodiments of this invention in which an exclusive property or privilege is claimed are defined as follows:

1. 2-[(2-dimethylaminoethyl) (p-methoxybenzyl)amino]pyridine 1,2,3,6-tetrahydro-1,3-dimethyl-2,6-dioxopurin-7-acetate.

* * * * *